(12) United States Patent
Testa

(10) Patent No.: US 6,358,255 B1
(45) Date of Patent: Mar. 19, 2002

(54) DISTRACTION OSTEOGENESIS DEVICE AND METHOD

(75) Inventor: Mauro Testa, Avigliano (IT)

(73) Assignee: Micerium S.r.l., Avegno (IT)

( * ) Notice: Subject to any disclaimer, the term of this patent is extended or adjusted under 35 U.S.C. 154(b) by 0 days.

(21) Appl. No.: 09/519,811

(22) Filed: Mar. 6, 2000

(51) Int. Cl.$^7$ .............................. A61F 2/36; A61C 3/00
(52) U.S. Cl. ......................... 606/105; 606/54; 606/59; 606/53; 433/7
(58) Field of Search .......................... 606/105, 53, 57, 606/60, 78, 70, 68, 69, 62, 58, 59, 170, 80, 54, 63, 64; 433/165, 166, 173, 7, 6, 17, 18, 19; 623/22.18, 22.37

(56) References Cited

U.S. PATENT DOCUMENTS

| | | | |
|---|---|---|---|
| 5,167,500 A | * | 12/1992 | Miura ........................... 433/7 |
| 5,364,396 A | * | 11/1994 | Robinson et al. ............. 606/53 |
| 5,785,520 A | * | 7/1998 | Carano et al. ................. 433/7 |
| 5,885,290 A | * | 3/1999 | Guerrero et al. .............. 606/71 |
| 6,162,223 A | * | 12/2000 | Orsak et al. ................... 606/59 |
| 6,187,004 B1 | * | 2/2001 | Fearon ......................... 606/57 |
| 6,203,548 B1 | * | 3/2001 | Helland ...................... 606/105 |
| 6,220,856 B1 | * | 4/2001 | Carano et al. ................. 433/7 |
| 6,267,589 B1 | * | 7/2001 | Farzin-Nia et al. ............ 433/7 |

* cited by examiner

*Primary Examiner*—Pedro Philogene
(74) *Attorney, Agent, or Firm*—Foley & Lardner

(57) ABSTRACT

A device especially for osteodistraction, configured for attachment to different bone parts that have been separated, and that are bound together by the device which holds the bones parts in a pre-set position and/or simultaneously exerts pressure for distancing or bringing together the bone parts. The device includes at least two elements configured for fastening to two bone parts that are separate from each other. The two elements are coupled together and movable along at least one pre-set direction, there being inserted between them an elastic element for providing a thrust in the distancing or traction direction. The device may be removably coupled to the bone parts to facilitate installation.

24 Claims, 12 Drawing Sheets

FIG. 1
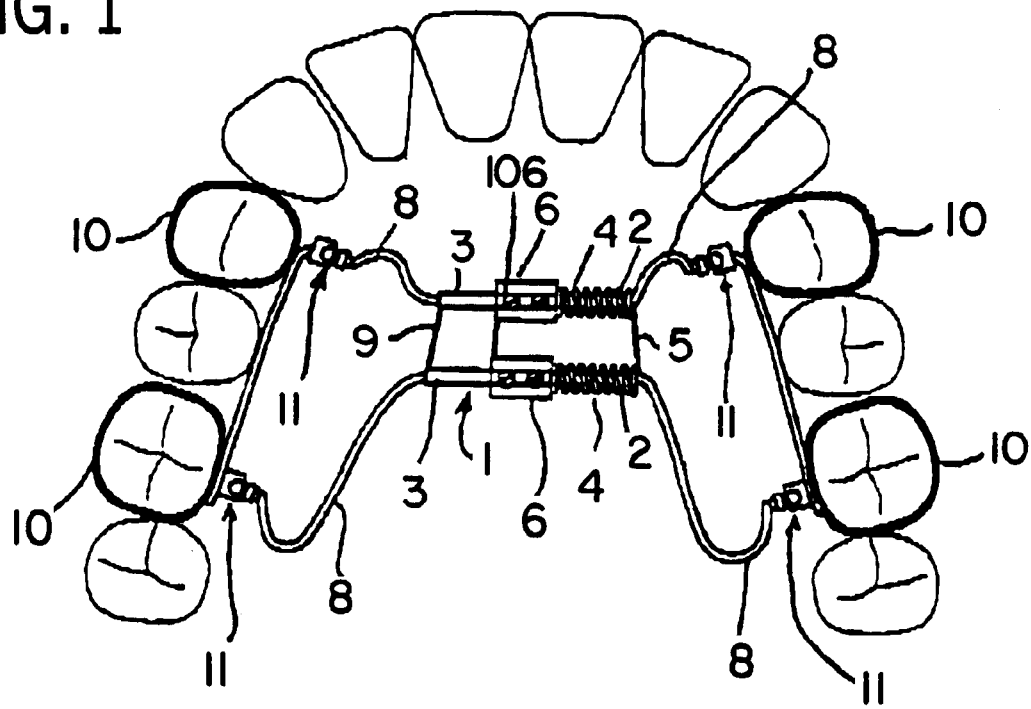
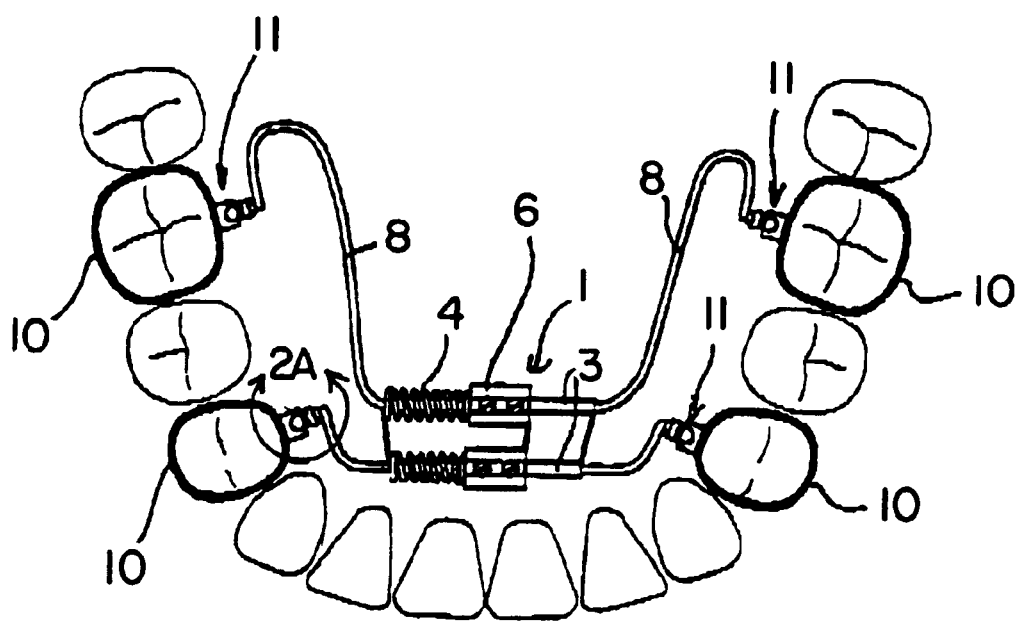
FIG. 2

FIG. 3
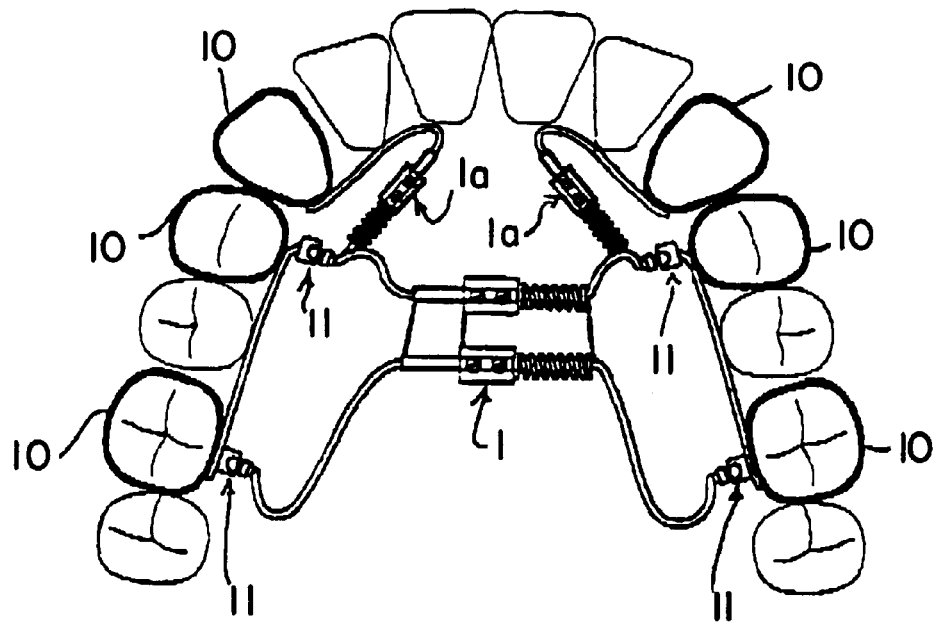
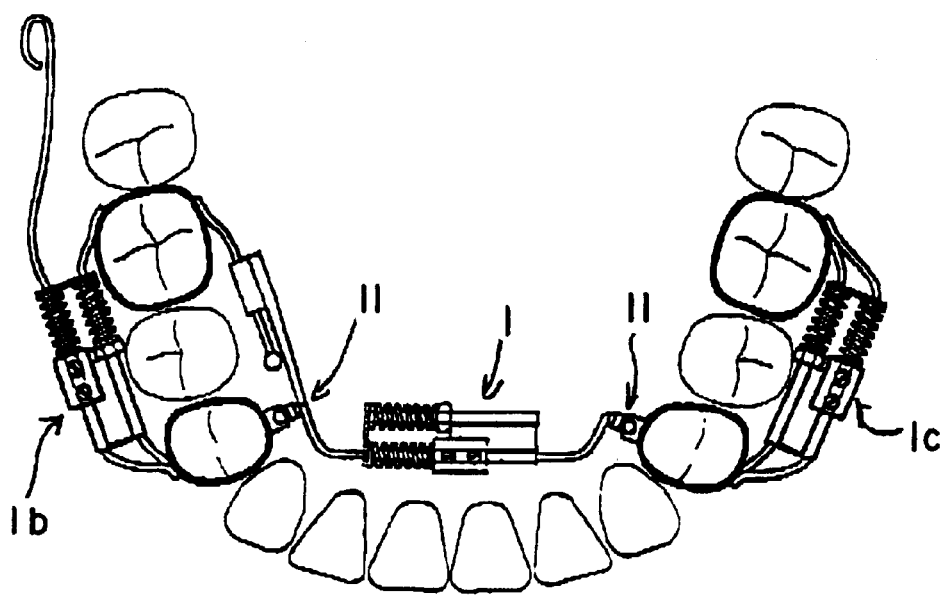
FIG. 4

DISTRACTION OSTEOGENESIS DEVICE AND METHOD

FIELD OF THE INVENTION

The present invention refers to a device especially for osteodistraction, that comprises means for anchoring to various bone parts, that are separate from one another or have been separated by sectioning, and that are bound together by mechanical means for holding the latter in a pre-set relative position and/or by the simultaneous pressure for the distancing or bring-together of these bone parts.

BACKGROUND OF THE INVENTION

Osteodistraction operations have as their purpose to stretch the bone, causing the formation of new bone tissue. To that end, the apparatuses for osteodistraction must be fastened, distant from each other, to bone zones that have first been separated, permitting the slight growth of the bone. Such an operation presents the advantage that it can be carried out as simple ambulatory operation, with local anaesthesia and without requiring the taking of any bone from the iliac crest, i.e., without risks.

At present, osteodistraction proves advantageous in cases of malformation and of orthopedic problems. A particular application is for the problems of nocturnal snorers, especially those subject to infarcts in sleep, and of tumor patients.

Presently, even though the technique is of course ambulatory, the devices and apparatuses for osteodistraction on the market are very bulky and especially traumatic. Some of the night devices are obtained, for some applications, in the form of an external device and therefore it is cumbersome from the standpoint of ambulatory treatment as well as from that of convenience and for its psychological effect on the patient.

Night devices have, in their simplest form, two fastening elements that are connected together by a spreading-apart/ bringing-together endless screw/nut device, or a pinion and rack device. Screw/nut or pinion/rack devices generally exert forces that vary from 4.5 to 9 kilograms. Such forces are appreciable and they exert a considerable pressure on the temporal mandibular articulation with effects that are not always foreseen.

A further limitation of the present devices results from the fact that they cannot operate vertically or in any case in compression, i.e., in such manner as to close spaces.

The purpose of the present invention is to obtain devices for osteodistraction operations with which it is possible to obviate the drawbacks of the night devices, permitting to obtain reduced sizes and weights, the exerting of distraction with more moderate forces and in a physiological manner that agrees better with the body and especially with tissues and articulations. The apparatuses according to the invention must be of easy and economical construction, and they must guarantee maximal operational flexibility for the different applications required.

SUMMARY OF THE INVENTION

The invention achieves the above-mentioned goals with a device for osteodistraction in operations of the type described at the onset, in which at least two fastening elements to two bone parts separate from each other are engaged together in a displaceable manner along at least one pre-set direction, there being inserted between these elements means for a thrust in the distancing or in the direction of distancing or of traction, i.e., in the bringing-together direction.

According to an improvement, these elastic means are provided in combination with means for imparting different loads to the elastic elements.

Generally, the two fastening devices may each present at least one guiding element that engages slidingly with that of the other fastening device, for example cylindrical elements telescopically displaceable relative to each other, such as a cylindrical tubular element and a guiding wire or pin.

The elastic element is made up of a spring inserted between radial joining elements of the two guiding members engaged in a sliding manner, of which at least one is axially displaceable along said guiding member and blockable into position on that guiding member itself, in a removable manner.

Advantageously, in order to exert a given force, it is possible for each fastening element to provide a pair of parallel guiding elements that engage slidingly with a corresponding element of the other fastening member, it being possible to provide for an elastic member (i.e., a traction or thrust spring) on each guiding element executed substantially according to the above-description.

The means for the variable loading of the springs can be separate for each pair of telescopic guiding elements, or they can be provided connected among themselves, in such manner that they can load the springs either differently or in a similar manner.

To permit a pressure in the compression direction (i.e., for the bringing-together of the two fastening elements), one of the guiding elements associated with one of these fasteners has means for the lengthening of the joining parts that cooperates with the elastic means in a position intermediate between the other fastening means and the corresponding radial joining element of the spring.

According to an improvement, the two telescopic guiding elements, slidable relative to each other, or other equivalent guiding means are executed as a separate and pre-fabricated construction element, and are equipped with means for being coupled, fastened or anchored to the fastening elements. This may be done for both end fasteners at the ends of the pair of guides as well as for one only of these fasteners, while the other one is assembled as one piece or fixed with the corresponding end of the pair of guides.

The fastening elements, in turn, may be double or triple fasteners that permit fastening or affixing to them two or more guides with their related elastic means, along two or more directions to exert the thrust or compression in two or more different directions.

A particular fastener is made up of two opposite elements hinged together, and each one of them is configured to be affixed to a sliding guide of a thrust or compression unit. The hinge makes it possible to orient the two connected thrust or compression units, in succession, along different axes. The hinge shaft or pin may be fixed, relative to the compression or traction directions, perpendicular, for example. The hinge, however, may also be in the form of a spherical joint or articulation, permitting relative angular positioning between the two thrust or compression units along other directions in the space.

A particular form of execution provides elements for direct fastening to the bone, for example to the mandibular bone. In this case, in the version in which the fastening elements are separate from the thrust or compression unit or units, a type of removable hooking or fastening of these two parts from each other can be of the coupling type, the fastening element provided being a couplable element such as a pin or pivot, and the pressure unit being provided with an articulation seat such as a segment of a cylindrical tubular element or the like, or vice-versa, which two elements (i.e., the articulation pivot and the corresponding cylindrical tubular element) being oriented transversely to the direction in which the thrust or compression is exerted.

For other applications, the means for anchoring the osteo-distraction unit or units are executed directly on the teeth. In this case, according to the invention, in order to permit physiologically correct displacements, especially with respect to the orientation of the teeth, the units are anchored to the fasteners by means of spherical coupling joints. The latter may be of the slip-hook type, or a simple free joint, and they are maintained in position by pressure forces of the thrust units, on the seats associated with the anchorings.

The spherical anchoring type, or the slip-hook type joints, with removable fixation, make it possible to obtain appreciable advantages by coupling. For example, in addition to the greater correctness of the distraction operation, relative to the physiological conditions, these devices, especially the different thrust or compression units, are easily removable whether as a combined unit or individually.

Thanks to the above-described units, it is possible to execute with great simplicity, and relatively economically and rapidly, an unlimited number of apparatuses for osteodistraction, that perfectly meet the requirements of the case and have an elastic action suited to the physiological requirements of the human body. These devices are very small, and they may be applied inside the oral cavity. They are light and exert forces that do not penetrate the bond structure nor the articulations. Furthermore, it being possible to vary the pressure of the elastic elements, when the growth of bone tissue has caused a displacement of the fastening elements themselves, by which the springs are unloaded, or when they exert insufficient pressure on the bone parts, it is possible to vary (i.e., to increase) the pressure of the springs to restore the distraction action. Over a certain range the pressures remain linear, without producing any peaks and not requiring too frequent adjustments.

Other improvements or variants of the invention constitute the object of the dependent claims.

BRIEF DESCRIPTION OF THE DRAWINGS

The invention will be better understood from the following description of the different forms of execution, illustrated as a non-limiting example, in the attached drawing in which:

FIGS. 1 to 4 illustrate a first form of execution of a thrust or compression unit for distraction devices, that are mounted in various osteodistraction apparatuses that have different functions.

DETAILED DESCRIPTION OF THE PREFERRED EMBODIMENTS

Figure 2A:
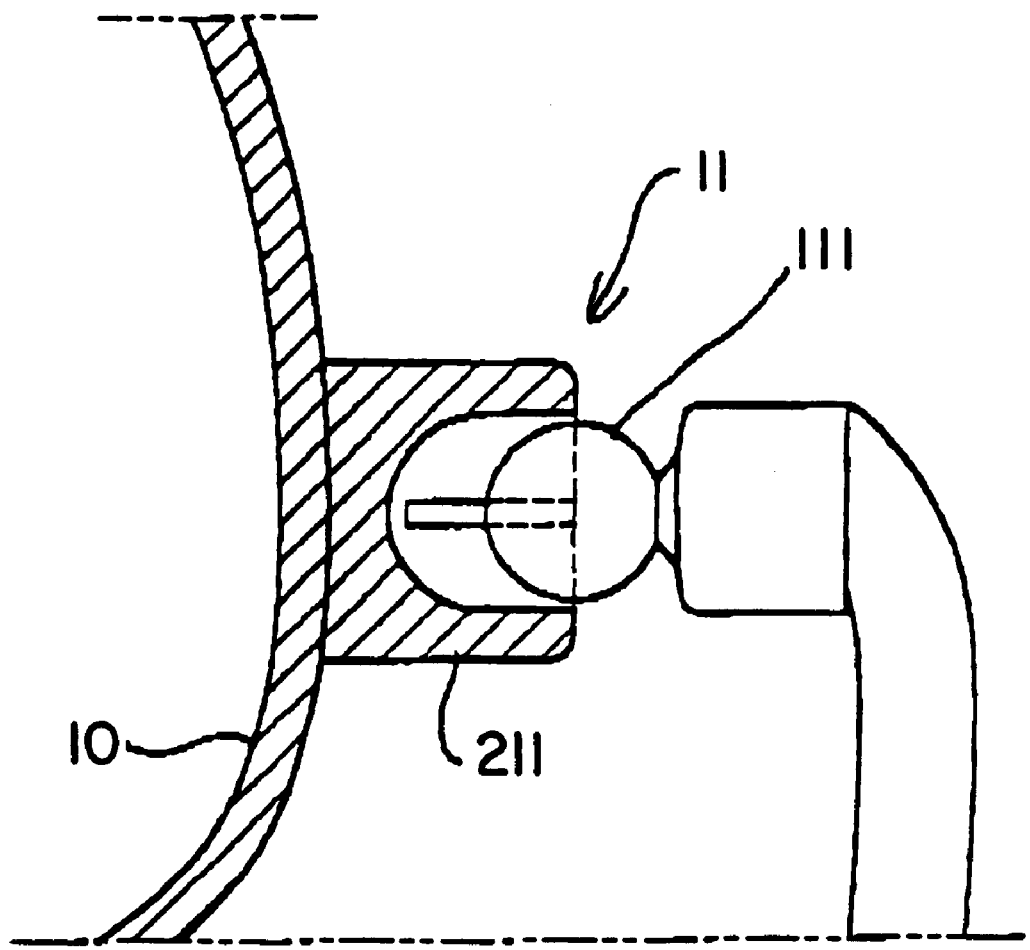
FIG. 2A illustrates an enlarged partial sectional view of a spherical coupling taken along line 2a in FIG. 2.

With reference to the Figures, an osteodistraction device is made up of a basic thrust or compression unit 1 that comprises two reciprocally slidable guiding elements 2, 3 that are subject to the action of a thrust or compression spring 4. These two elements comprise a guiding stem or peg 2 and a cylindrical element 3, such as a cylindrical tubular element inside which the peg or stem is axially and telescopically slidable.

Obviously, it is possible to provide for more than two reciprocally slidable elements. Both of the guiding elements 2, 3 are provided with radial joining elements 5, 6 between which there is inserted the helix-shaped spring 4. Advantageously, one of the radial joining elements, preferably element 6 engaged on the tubular element 3, is made movable therealong and blockable in a pre-set axial position, while element 5 engaged on guiding element 2 is fixed in position. Preferably, movable element 6 is made up of a small socket provided with radial screws 106 for tightening on the cylindrical tubular element 3 or on the guiding element 2 associated with it.

Thanks to this characteristic, it is possible either to turn off the thrust force or to re-establish it when the distraction action has produced a displacement of the bone parts in the desired direction, with a loss of load in the spring 4.

To obtain a bringing-together or a compression force, it suffices that, to the guiding pin 2 there be associated a joining element 107 (see FIG. 12) mounted on a supporting pin 7 that starts at the external end of guiding pin 2 and extends to the joining sleeve 107 at its free end. The length of support pin 7 is such as to permit the joining sleeve 107 to become slidingly engaged on the cylindrical tubular element 3 in a position posterior to that of the radial joining of same (i.e., posterior to that of the blocking socket 6), with reference to the external end of the guiding pin 2. Obviously, such construction can be inverted, providing that the support pin 7 with the joining sleeve 107 is associated with the cylindrical element 3, while the radial movable joining element 6 is mounted on the guiding pin.

The free opposite ends of the guiding pin 2 and of the cylindrical tubular element 3 are fixed, or fixable, in any desired manner to an anchoring structure that may be actuated by anchoring to one or more teeth and/or, alternately or in combination, to one or more bone parts, especially a mandibular bone part.

In the forms of execution in FIGS. 1 and 2, the basic unit is provided in double, in an apparatus for the distraction of the palate. In these apparatuses, the two cylindrical tubular elements 3 and the two springs 4, as well as the two joining sockets 6 blockable in position, are connected among themselves by transverse elements 9, and extended by means of elements 8 toward the anchoring 10 of the teeth.

The fastening of the thrust or compression unit is done by means of spherical joints or articulations 11 that permit the teeth freely to take a correct orientation, with the progressive distraction of the palate.

Each connecting or extension element 8 has at its end a small sphere 111 (see FIG. 2A), while the anchoring elements 10 have, on their side turned toward the double thrust and/or compression unit, a spherical seat 211, or even also a spherical sector that engages on the small sphere.

The apparatuses in FIGS. 3 and 4 constitute variants in execution of the apparatuses according to FIGS. 1 and 2, in which, in addition to a distraction action in the direction of the palate divisions (i.e., transversely to the antero-posterior axis), the apparatuses also exert an action along a component parallel to the antero-posterior axis that is developed by means of one or two further double basic units, indicated by 1a, 1b, 1c.

The thrust or compression units 1 may also present other types of fixation to the anchorings 10, that may be articulated along one or more axes, or may also be rigid fixations, i.e., without any degree of freedom between anchoring element 10 and the thrust or compression unit 1.

Figure 5:
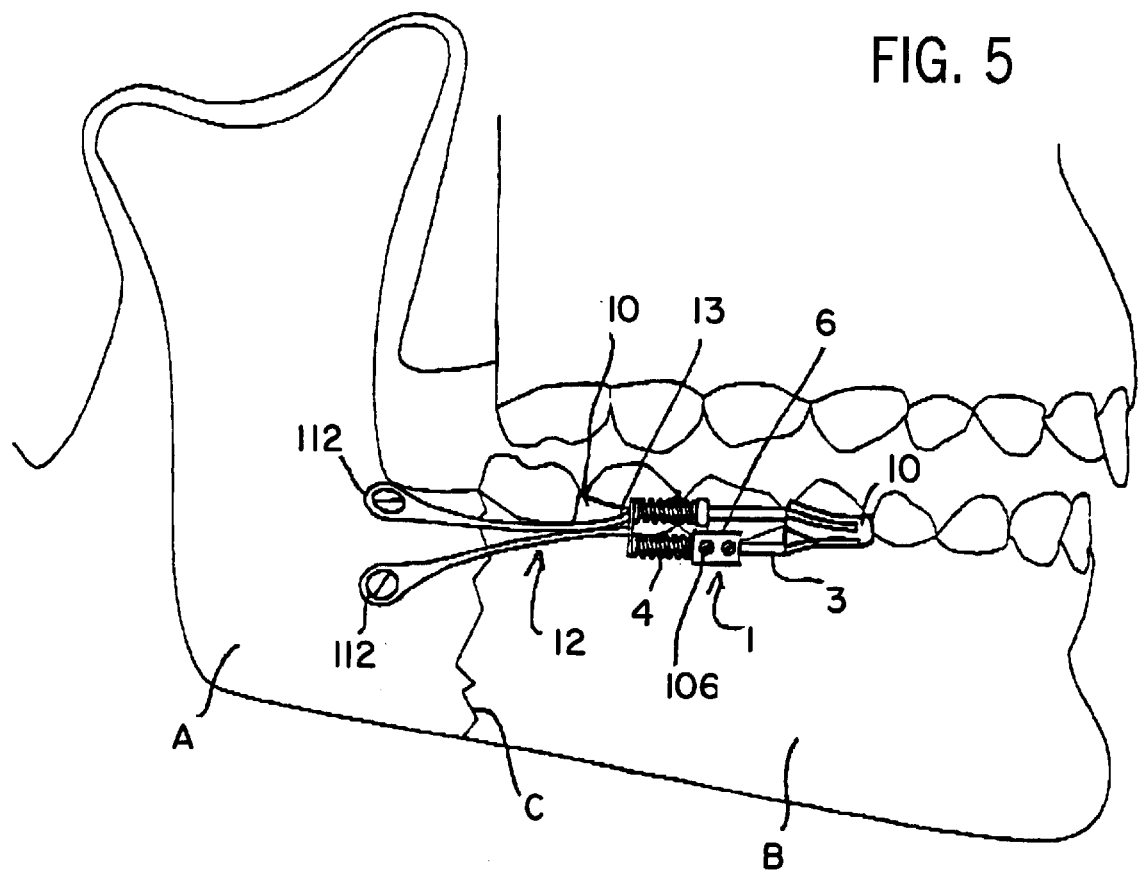
FIGS. 5 and 6 illustrate a further form of execution of the invention.
Figure 6:
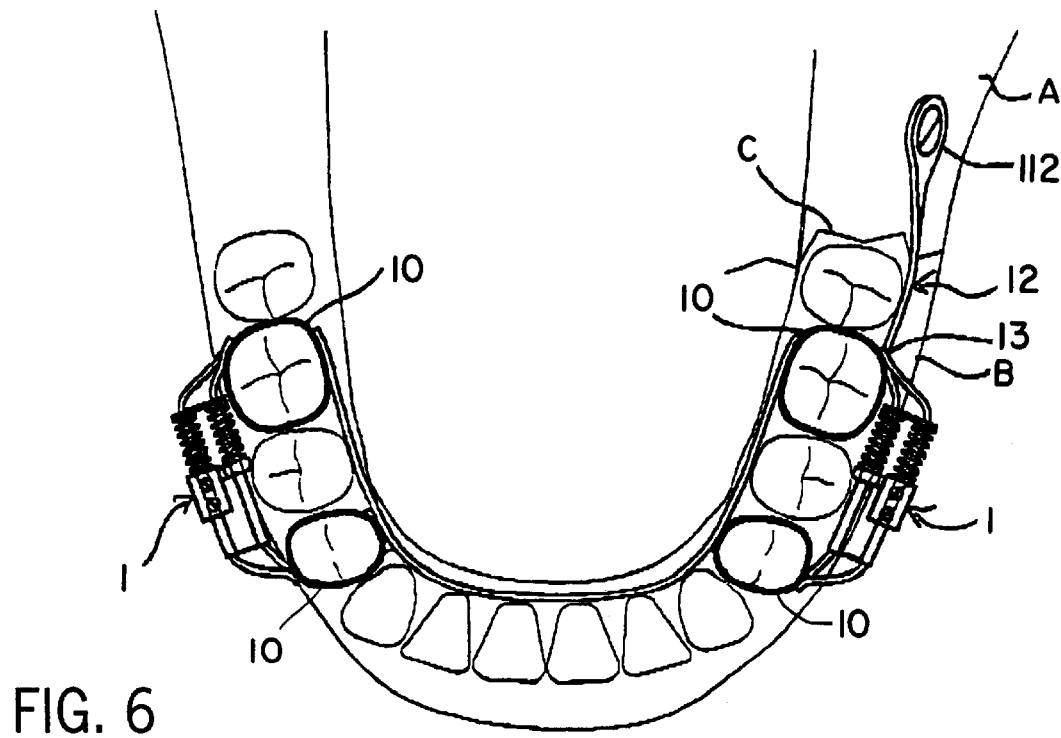

With reference to FIGS. 5 and 6, and to the remaining FIGS. 7 to 12, the elastic thrust and/or compression unit 1, either in its simple or in its double form, can be anchored, directly as well as through a transmission element, to one or to two bone parts.

In the case of FIGS. 5 and 6, there is attached to the anchoring 10 of the tooth a fixation and/or transmission element to a part of the mandibular bone A that is separated from the part B with which the tooth anchoring element 10 is associated, by a fracture or sectioning line of the bone, indicated by C. In this case, the fixation to bone A is done by means of screws that engage into one, preferably into two, tightening small eyes placed at a distance from each other relative to the direction perpendicular to the thrust direction. The direct anchoring or fixation to the bone is indicated by 12, and the related small eyes are indicated by 112, which in the case of FIGS. 5 and 6, the fixation to the anchoring element of the tooth is indicated by 13.

In FIGS. 7 and 7A–7C there is provided a thrust and compression unit 1 with a double pin 2 and a double cylindrical tubular element 3, the construction of which substantially corresponds to that describe above. In this case, the double displaceable socket 6, for the joining or for the loading of spring 4 has the screws 106 for the blocking into position only on one of the sockets associated with one of the two cylindrical tubular element 3, while the other one is rigidly connected to the other element by a cross piece 206.

Figure 7:
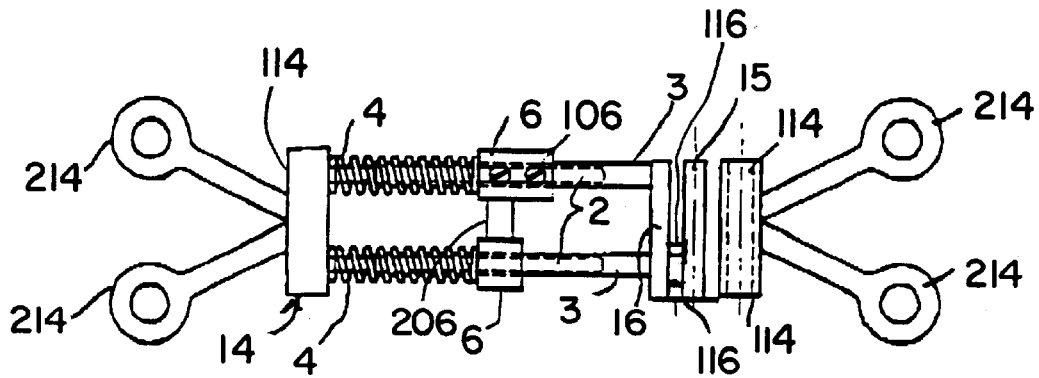
FIG. 7 illustrates an enlarged view of a simple pressure or compression unit having removable end fasteners.
Figure 7A:
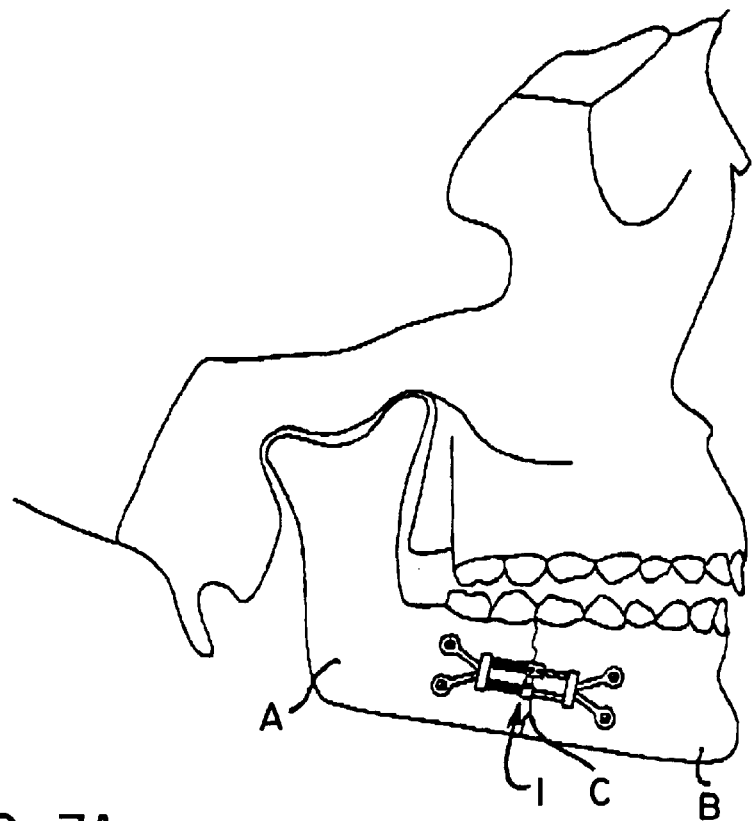
FIGS. 7A–7C illustrate the unit in FIG. 7, applied to the mandibular and maxillary bones.
Figure 7B:
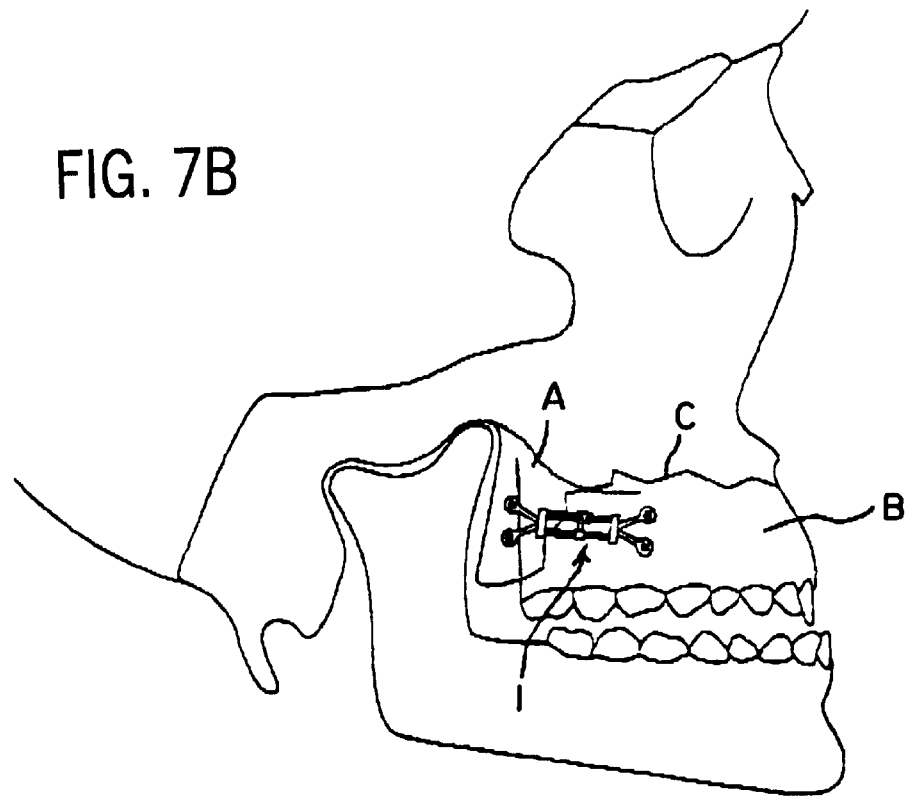
Figure 7C:
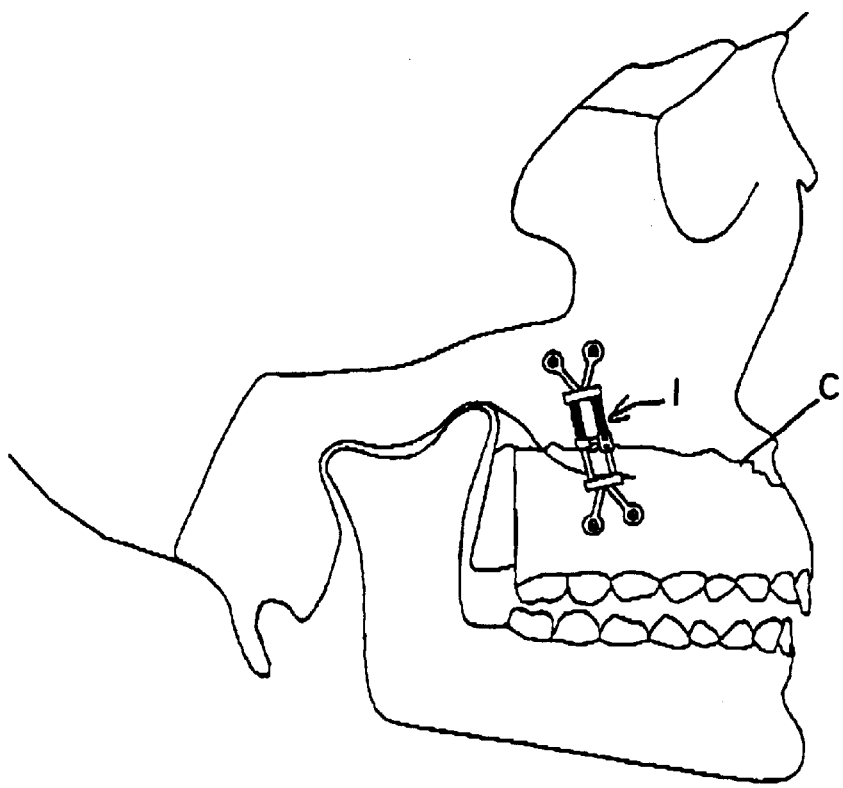

The ends of the guiding cylindrical tubular elements 3 and of the sliding pins 2 opposed to one another are connected by cross piece 114 of the fixation elements 14 of the double thrust and/or compression unit 1, directly to two bone parts A, B, adjacent and separated by a sectioning or break line C (see FIGS. 7A–7C).

The cross piece 114 can be directly affixed, in a stable manner, to the corresponding cylindrical tubular element 3 and to the sliding pin 2, and they present at their opposite ends two small fixation ears 214 that form the small eyes for fixation by means of screws.

According to a preferred form of execution, the anchoring element 14 at one end at least, if not at both ends, can be coupled in a removable manner to the thrust and/or compression unit 1 (see FIG. 7).

In this case, the cross piece 114 with the two small ears 214 is slightly separated and this cross piece 114 is made up of a coupling sleeve the internal section of which preferably is not round, and in which there is meant to be engaged a coupling pin 15 of corresponding section, carried by a cross piece 16 connecting the corresponding ends of the cylindrical tubular element 3 or of the sliding pin 2. Coupling pin 15, preferably not round either, is affixed to the cross piece 16 in correspondence with one end so as to prevent the need for a continuous split (fissure) on the coupling sleeve 114, that at the limit must have, possibly but not necessarily, a partial slit for the passage of the small fixation poles 116 securing the coupling pin 15 to cross piece 16.

There must be noted the extreme simplicity of the thrust and/or compression unit and the compactness of same, as well as the fact that it can easily be used for a second distraction in either direction, vertical or horizontal. The assembling work is most simple and, thanks to the fact that it presents removable coupling means, especially of the engaging type with one, two, or more of the anchoring elements 14 provided, it affords a great ease of work for the surgeon who can mount the compression and thrust unit immediately after having fixed the anchoring means 14 and performed the bone sectioning.

Figure 8:
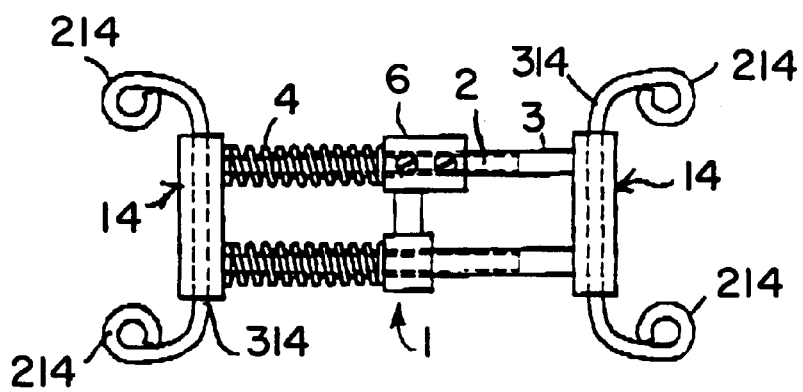
FIG. 8 illustrates an enlarged view of a simple pressure or compression unit having simplified end fasteners.
Figure 8A:
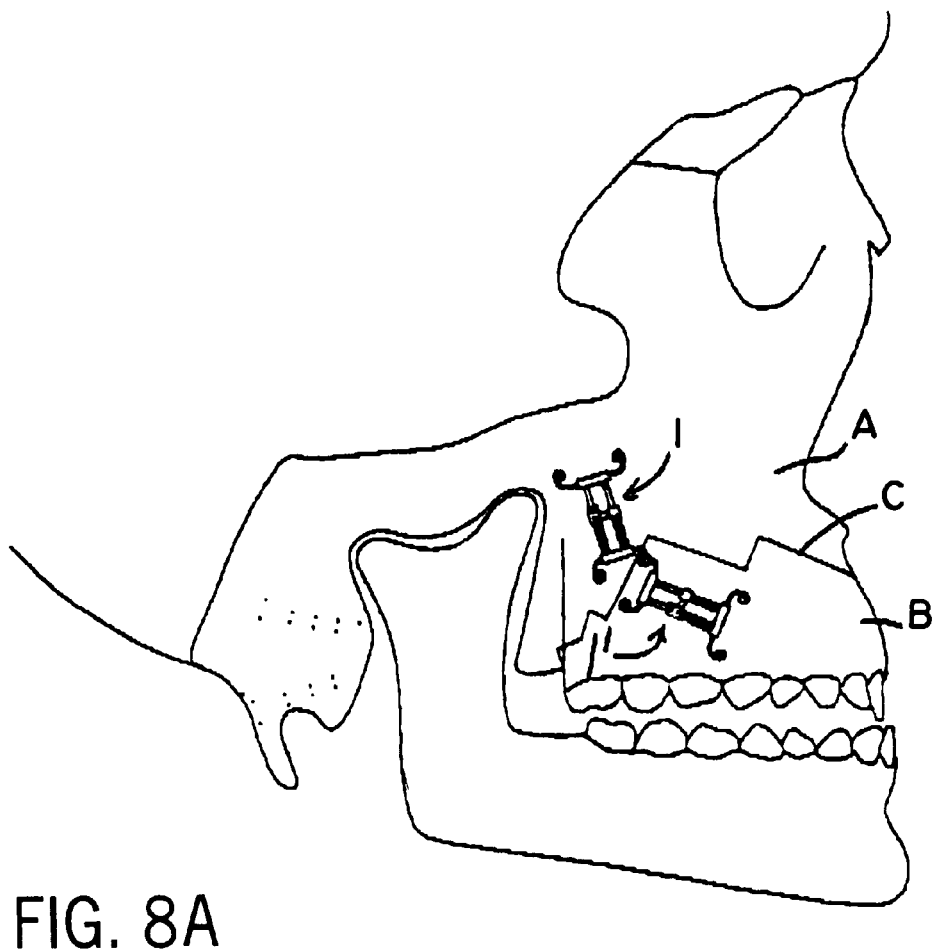
FIG. 8A illustrates a pair of the unit in FIG. 8, applied to the maxillary bone in series and oriented in two different directions.

FIGS. 8 and 8A show a variant of execution of an apparatus for distraction, one arranged for work on different bone parts, along two different directions. In this case, the ear-shaped parts 214 of each anchoring element 14 are formed by a continuous wire 314 that is not removable once it is appropriately bent to provide the faster loops. In this case, two identical units 1, 1' are arranged in succession, and one of the anchoring ear-shaped parts 214 of an anchoring element 14 is affixed to one of the ear-shaped parts 214 of an adjacent anchoring element 14 of the other thrust and compression unit 1'. The remaining anchoring ear-shaped parts 214 of each unit 1, 1' are secured by screws to respective bone parts A, B, to obtain distraction actions therebetween.

Figure 9:
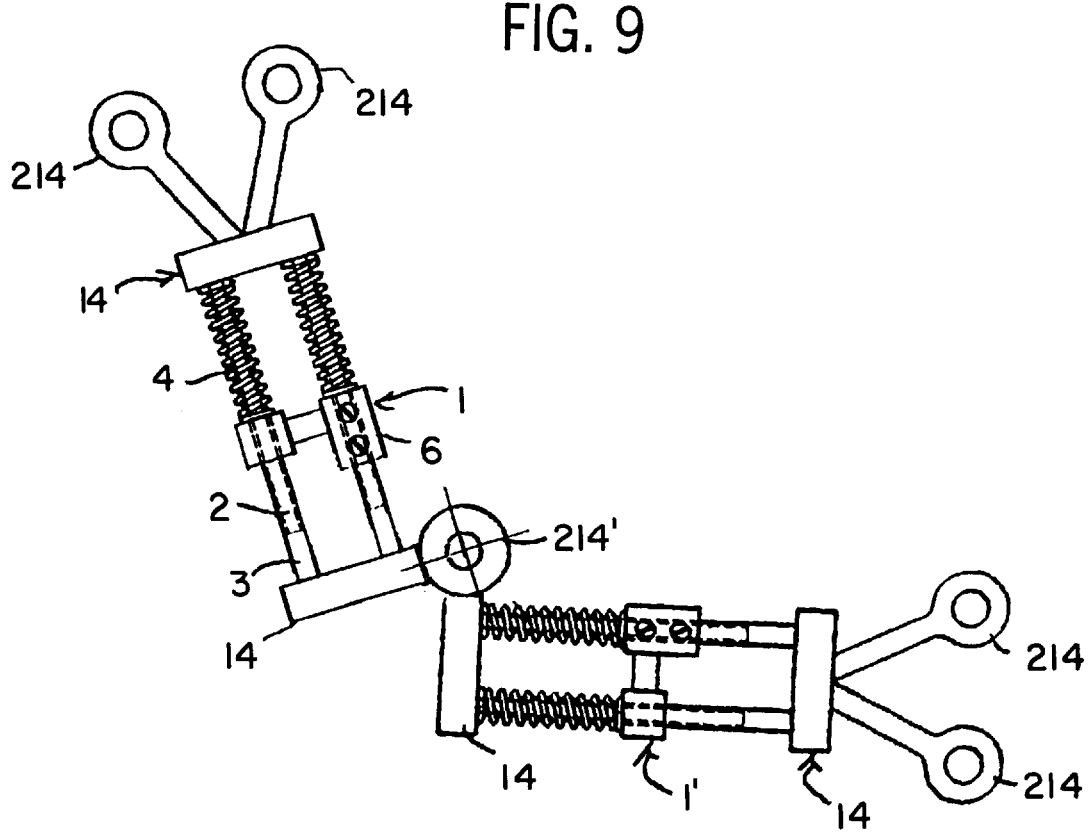
FIG. 9 illustrates an enlarged view of an apparatus formed of two of the units in FIG. 7, mounted in series and oriented about a pivot hinge in two different directions.
Figure 9A:
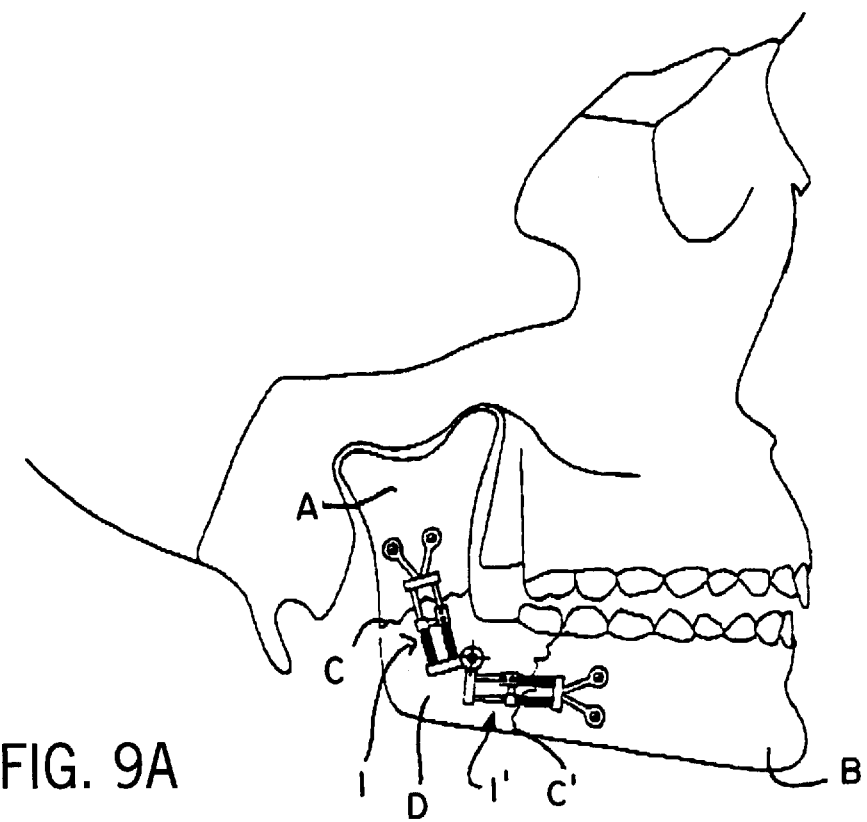
FIG. 9A illustrates the unit in FIG. 9, applied to the mandibular bone.
Figure 10:
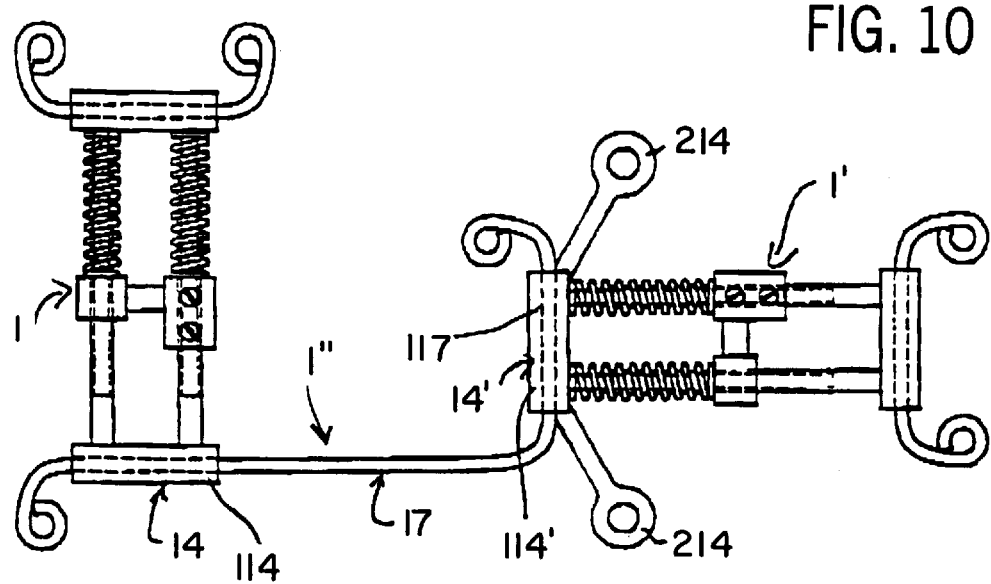
FIG. 10 illustrates an enlarged view of an apparatus formed with a pair of thrust units joined together and oriented in perpendicular directions.
Figure 10A:
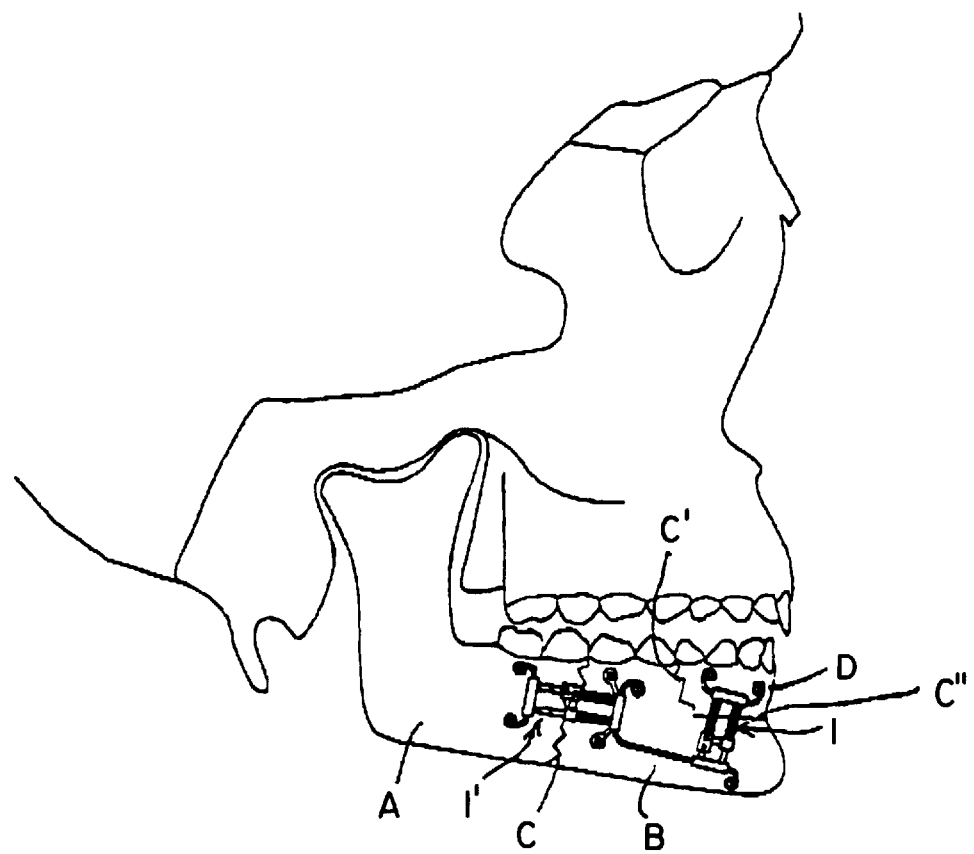
FIG. 10A illustrates the apparatus in FIG. 10, applied to the mandibular bone.
Figure 11:
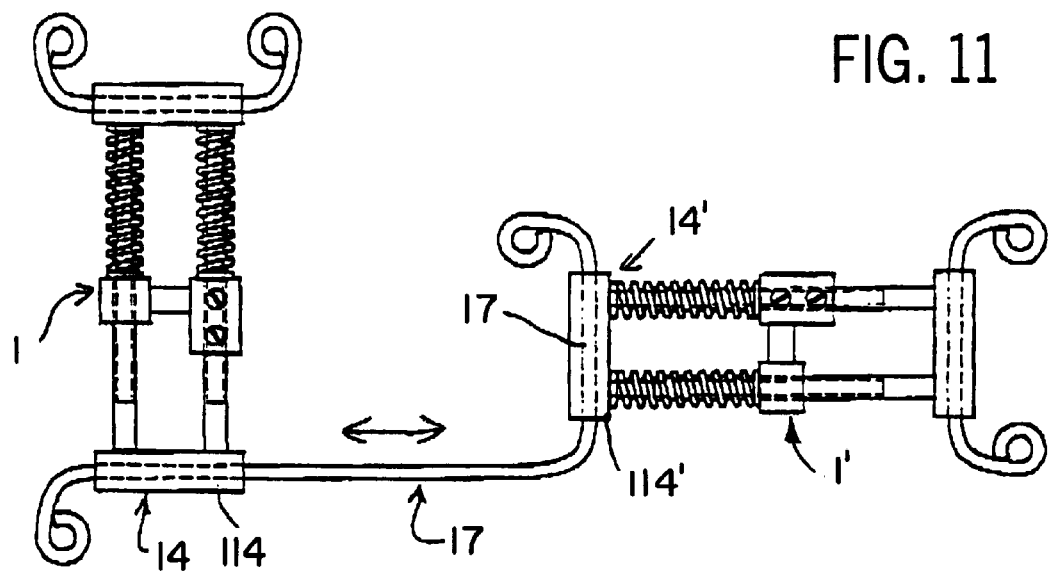
FIG. 11 illustrates an enlarged view of an apparatus similar to the unit shown in FIG. 10, but having simplified end fasteners.
Figure 11A:
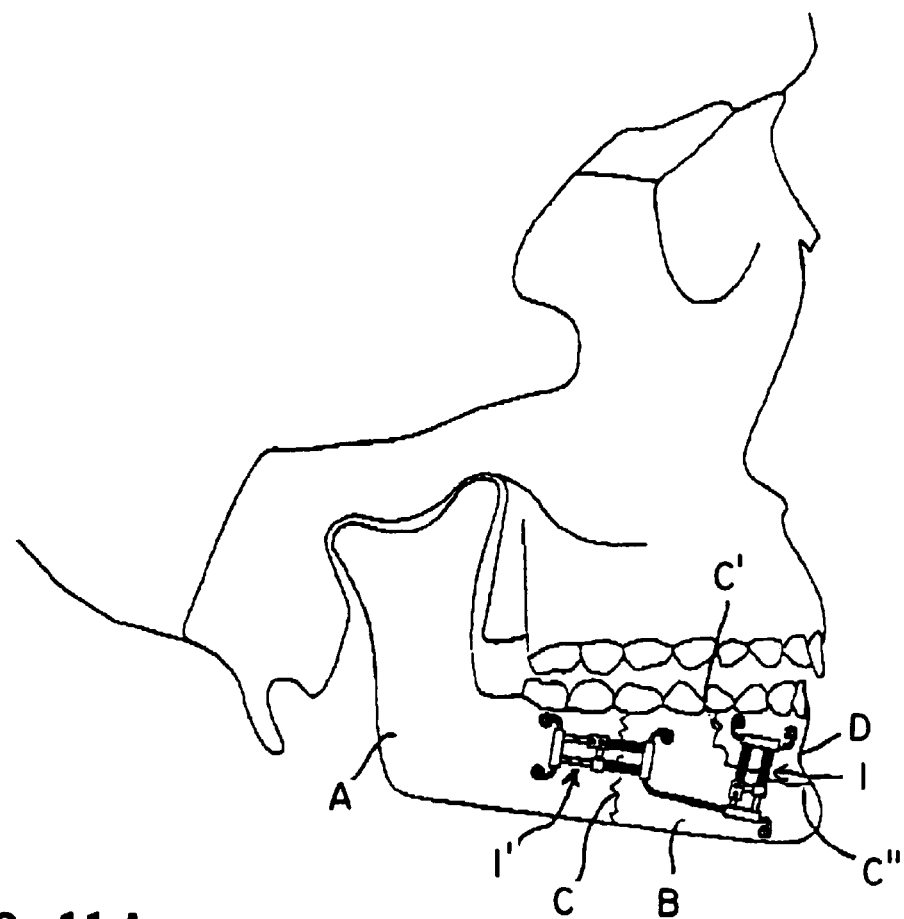
FIG. 11A illustrates the apparatus in FIG. 11, applied to the mandibular bone.

As shown in FIGS. 9 and 9A, the indicated articulation anchoring elements of two units 1, 1' may also be executed, advantageously, with a single ear-shaped hinging and fixation small ear 214'.

In this case, the fixation to bone D that is made up of an intermediate segment between two other bone parts, A and B, separated from the first one by the separation lines C, C', is obtained by means of a single common screw that also forms a hinge pin around which it is possible to rotate the two units 1, 1' in order to obtain distraction actions of the part A with respect to part D, and of part B relative to part D in different directions and substantially perpendicular to separation lines C, C'.

According to a variant in execution, the hinge pin need not necessarily be a screw for fixation to bone D, but it may also be a hinge pin that is mounted ahead of time and that is free from the bone part D laying under it.

The articulation illustrated with reference to FIGS. 8, 8A or 9, 9A permits an orienting of the two units 1, 1', along an axis perpendicular to the thrust and compression axis along which the latter are acting. It is also possible, however, to provide for other types of hinges, that make it possible to orient the two units 1,1' between them along other directions.

FIGS. 10, 10A and 11, 11A illustrate further improvements of the invention, that permit the execution of a distraction apparatus combined according to two perpendicular directions.

In each case the bone is subdivided, by a suitable sectioning operation, into three parts A, B, D, respectively separated by an approximately vertical straight line C and by a line forming angle and having a segment C' substantially vertical and parallel to line C, and a transverse segment C". The bone part D must be moved either vertically only, or both vertically and horizontally.

In each case there are provided two double thrust units 1, 1' while a further thrust unit 1" is integrated with an element for the removable connection between 1 and 1'.

These units 1, 1' are schematically shown and they present a construction substantially similar to that described above. The indicated anchoring elements 14, 14' to be connected together have respective coupling sleeves 114, 114' for the inserting of an intermediate connection element 17, advantageously executed as an elbow. One end 117 constitutes the coupling pin in the coupling sleeve 114' of a unit 1', while the other end 217 may constitute a guiding pin sliding inside the sleeve 114 of the other unit 1, thus forming therewith the guiding tubular element/sliding pin pair of the further thrust unit 1", a simple one this time. In this case, other constructive parts of the thrust unit 1" obviously would be present (e.g., blockable sockets and springs), since all of the thrust or compression units, whether simple or double, are executed substantially according to the same principle.

The slanted intermediate element 17, as illustrated in each case, may alternatively form only a rigid connection element, i.e., its other end 217 being also executed in the form of a simple coupling pin. In this case, a thrust action of bone D in direction of this end 217 is not necessary, but only a precise angular and nonvariable positioning of the two units 1, 1' respectively to each other, permitting at the same time an important distancing of these two units 1, 1' according to the requirements dictated by the structure, the shape and the size of the bone part A, B, D.

Figure 12:
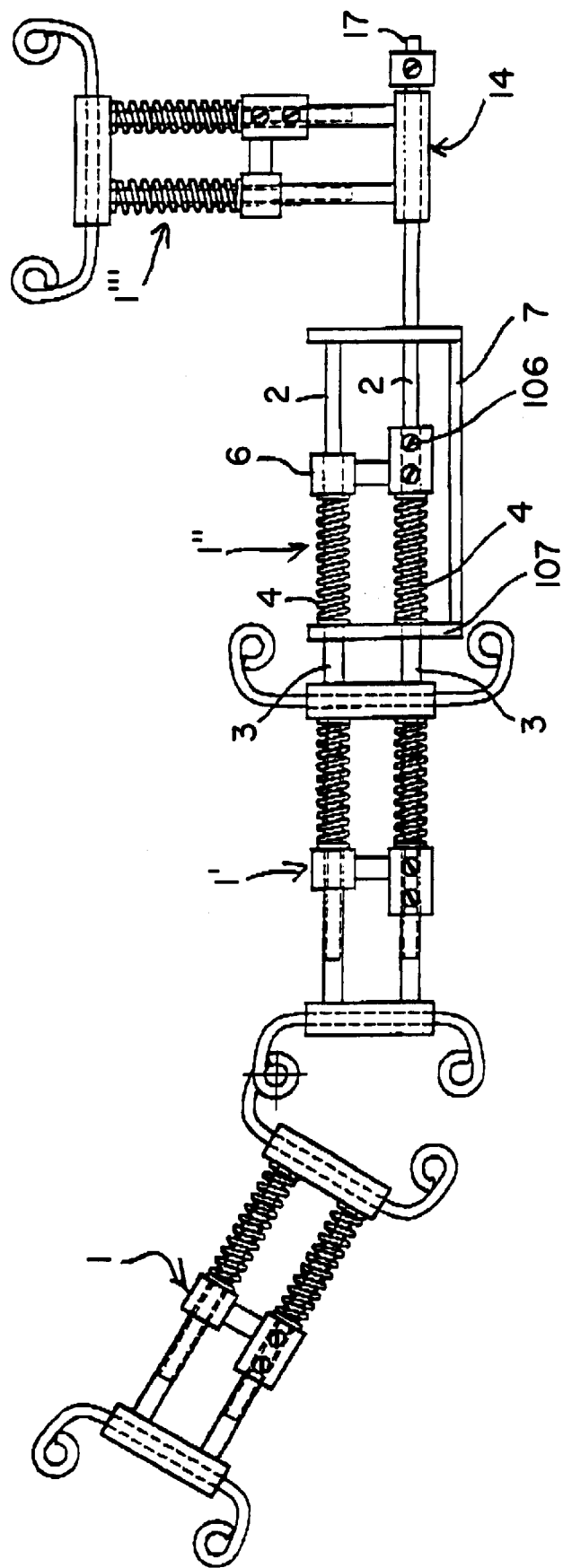
FIG. 12 illustrates an enlarged view of a compression unit mounted in series with other units, including one unit configured for compression and other units oriented in different directions.
Figure 12A:
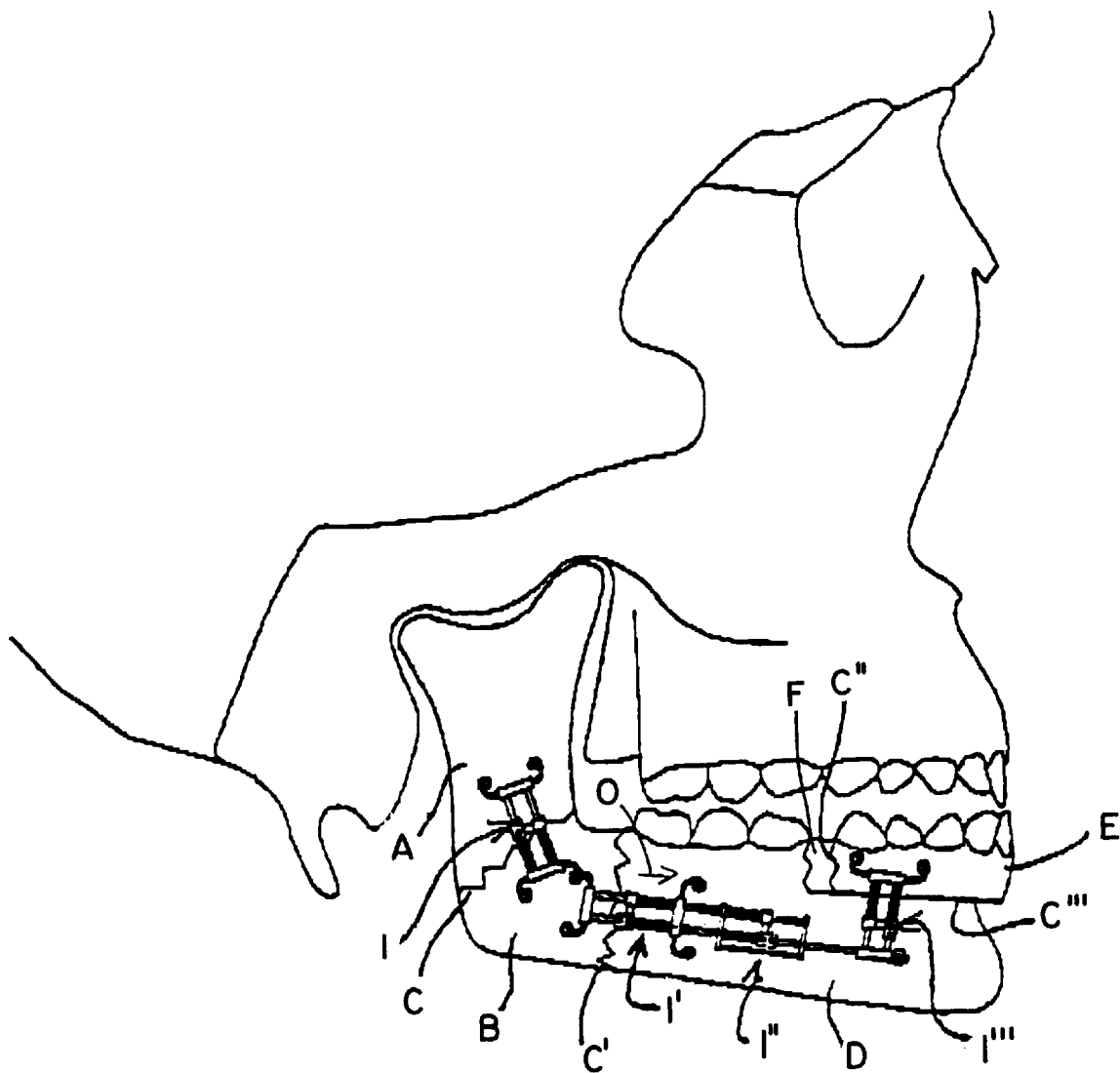
FIG. 12A illustrates the apparatus in FIG. 12, as mounted on the mandibular bone.

FIGS. 12 and 12A illustrate a further variant in execution of an apparatus for osteodistraction, executed by coupling together several thrust and compression units according to the invention. In this case, it is a matter of performing a complex and composite distraction of four bone parts A, B, D, E. In this case, the problem is a combination of the operations according to FIG. 9 and according to FIGS. 11 and 12. The difference consists in that, instead of part E having to be thrust away from part D, with respect to the horizontal direction (indicated by arrow O) it must be brought closer to the latter, assuming a position of the bone part F that has been removed.

The osteodistraction unit illustrated in FIGS. 12 and 12A therefore comprises the combination, in succession, of four units 1, 1', 1", 1'". Unit 1 and unit 1' are executed in the form of two thrust units connected together by means of an articulation, in a manner similar to FIGS. 8, 8A and 9, 9A. Unit 1" is rigidly connected to unit 1' and it is executed in the form of a compression unit, as already described above, and unit 1'" is rigidly connected to the latter in a fixed transverse orientation, especially a perpendicular one, and it is executed in the manner of a thrust unit.

The coupling of the single units among themselves, regardless whether the version dealt with is meant for distancing thrust or bring-together compression, may be as described above, articulated as well as fixed or removable.

Obviously, the construction characteristics illustrated with reference to the individual examples of execution can be freely combined with one another, thus adapting the compression and/or thrust units 1 according to the invention to the various therapeutic and morphologic requirements.

The examples illustrated demonstrate the great versatility and the simplicity, as well as the economy of use, of the device according to the invention that, starting from the most simple functional elements permits the execution of complex structures with a substantially modular construction. Their extreme lightness and compactness permit to avoid external applications and render the surgeon's work easier and simpler. Also, the fact of providing for fasteners or hooks of the removable type greatly simplifies the work of the surgeon.

The pressure exerted by means of the elastic elements (i.e., the springs), makes it possible to apply the force necessary in the most harmonious and less rigid, as well as physiologically less traumatic, manner, thus improving the therapeutic function of the distraction apparatuses.

The invention of course is not limited to what has been described and illustrated, but it may be varied, especially in its construction and arrangement of units.

Thus for example, the particular means for hooking the anchoring elements, whether removable, articulated or fixed, the elasticity-regulating means, and the guides for reciprocal sliding, as well as the springs, may be made in any way. Furthermore, the construction characteristics of the thrust and compression units may be extended to any type of apparatus, such as for example an apparatus for orthodontics, or orthopedics or the like. All of this without giving up the characterizing principles presented above and claimed below.

What is claimed is:

1. A device for dental or oral osteodistraction of at least two different bone parts that are separated from one another, comprising:

anchoring means for fastening the device to the separated bone parts of the mandible or maxilla; and mechanical means for holding the different bone parts in a pre-set position and for simultaneous exerting pressure for distancing or tractioning the different bone parts, the mechanical means including at least two guiding elements movably coupled together according to at least one pre-set direction and configured for fastening at opposed ends to the anchoring means, there being inserted between the opposed ends an elastic means for applying a thrusting force in one of the distancing and tractioning directions.

2. A device according to claim 1, wherein the elastic means is provided in combination with means for varying the thrust loading of the elastic means.

3. A device according to claim 1, wherein the two guiding elements comprise a cylindrical tubular element slidably movable relative to a guiding wire of a pin element telescopically received therein.

4. A device according to claim 3, wherein the elastic means comprises a spring inserted between two radial joining elements of the two telescopically engaged guiding elements, of which at least one of the joining elements is axially movable along its guiding element and blockable in a removable manner into position thereon.

5. A device according to claim 4, wherein the mechanical means provides a tractioning force, and one of the guiding elements has an extension of the associated joining element that cooperates with the elastic means in intermediate position between the two joining elements to provide the tractioning force.

6. A device according to claim 3, wherein the two telescopically engaged guides are executed as a separate and pre-fabricated construction unit.

7. A device according to claim 1, wherein the at least two guiding elements comprise at least two pairs of telescopically sliding guides having relative elastic and configured to exert thrust or compression forces along at least two different directions.

8. A device according to claim 7, wherein the anchoring means includes a particular fastener for securing the at least two pairs of telescopically sliding guides, the particular fastener providing a hinge shaft being set relatively at an angle to at least two different directions.

9. A device according to claim 1, wherein the anchoring means provides for the end of at least one of the guiding elements to be affixed directly to the bone part.

10. A device according to claim 1, wherein the anchoring means provides for the end of at least one of the guiding elements to be removably coupled to the bone part.

11. A device according to claim 10, wherein the at least one removable coupling is of the in-fitting, hinge or articulation type, and that is many-directional and allows relative orientation of the associated guiding element along one or more articulation axes.

12. A device according to claim 10, wherein the at least one removable coupling comprises an insertable element provided by one of the guiding element and the anchoring means and a corresponding insertion seat provided on the other of the guiding element and the anchoring means.

13. A device according to claim 12, wherein each insertable element is a pin or peg and each insertion seat is a cylindrical tubular element.

14. A device according to claim 1, wherein the anchoring means for the thrust or compression device is executed at least in part directly on teeth associated with the different bone parts.

15. A device according to claim 1, wherein the device is coupled to a similar device by an interconnection means which itself is configured like the devices.

16. A device for osteodistraction of at least two different bone parts that are separated from one another, comprising:
   anchoring means for fastening the device to the separated bone parts; and
   mechanical means for holding the different bone parts in a pre-set position and for simultaneous exerting pressure for distancing or tractioning the different bone parts, the mechanical means including at least two guiding elements movably coupled together according to at least one pre-set direction and configured for fastening at opposed ends to the anchoring means, there being inserted between the opposed ends an elastic means for thrusting in the distancing or tractioning direction,
   wherein each guiding element comprises a pair of parallel guides that engage in a telescoping manner with a pair of corresponding guides of the other guiding element, and wherein the elastic means is associated with each of the telescopically engaged guides.

17. A device according to claim 16, wherein the means for the varying the loading is separate for each of the telescopically engaged guides so that each can be loaded in a different amount.

18. A device according to claim 16, wherein the means for the varying the loading is common to the telescopically engaged guides so that each is loaded in a like amount.

19. A device for osteodistraction of at least two different bone parts that are separated from one another, comprising:
   anchoring means for fastening the device to the separated bone parts; and
   mechanical means for holding the different bone parts in a pre-set position and for simultaneous exerting pressure for distancing or tractioning the different bone parts, the mechanical means including at least two guiding elements movably coupled together according to at least one pre-set direction and configured for fastening at opposed ends to the anchoring means, there being inserted between the opposed ends an elastic means for thrusting in the distancing or tractioning direction,
   wherein the at least two guiding elements comprise a single pair of telescopically sliding guides.

20. A device for osteodistraction of at least two different bone parts that are separated from one another, comprising:
   anchoring means for fastening the device to the separated bone parts; and
   mechanical means for holding the different bone parts in a pre-set position and for simultaneous exerting pressure for distancing or tractioning the different bone parts, the mechanical means including at least two guiding elements movably coupled together according to at least one pre-set direction and configured for fastening at opposed ends to the anchoring means, there being inserted between the opposed ends an elastic means for thrusting in the distancing or tractioning direction,
   wherein the anchoring means provides for the end of at least one of the guiding elements to be removably coupled to the bone part, the at least one removable coupling comprises an insertable element provided by one of the guiding element and the anchoring means and a corresponding insertion seat provided on the other of the guiding element and the anchoring means, and each insertable element is a spherical ball and each insertion seat is a spherical seat.

21. A device for dental or oral osteodistraction of at least two different bone parts that are separated from one another, comprising:
   anchoring means for releasably coupling the device to the separated bone parts of the mandible or maxilla directly or to teeth associated with the bone parts; and
   mechanical means for holding the different bone parts in a pre-set position and for simultaneous exerting pressure for distancing or tractioning the different bone parts, the mechanical means including at least two guiding elements movably coupled together according to at least one pre-set direction and configured for releasable fastening at opposed ends to the anchoring means, there being inserted between the opposed ends an elastic means for applying a thrusting force in one of the distancing and tractioning directions.

22. A method for dental or oral osteodistraction of at least two different bone parts using a device that includes anchoring means for securing the device to the different bone parts and mechanical means for holding the different bone parts in a pre-set position and for simultaneous exerting pressure for distancing or tractioning the different bone parts, the method comprising the steps of:
   securing the anchoring means to the different bone parts of the mandible or maxilla;
   sectioning the different bone parts; and
   coupling the mechanical means to the anchoring means to apply a thrusting force to the sectioned bone parts in one of the distancing and tractioning directions.

23. A method according to claim 22, wherein the anchoring means includes insertion seats and the mechanical means includes corresponding insertable elements, and wherein the coupling step comprises inserting the insertable elements into the insertion seats.

24. A method according to claim 23, wherein the mechanical means includes at least two elongated guiding elements telescopically coupled together according to at least one pre-set direction and having opposed ends configured for releasable coupling to the anchoring means, and wherein the coupling step comprises collapsing the at least two elongated guiding elements together to position the opposed ends adjacent the anchoring means, and then untelescoping the at least two elongated guiding elements.

\* \* \* \* \*